(12) United States Patent
Shankarsetty et al.

(10) Patent No.: US 11,666,329 B2
(45) Date of Patent: *Jun. 6, 2023

(54) SURGICAL STAPLING INSTRUMENT WITH CURVED END EFFECTOR

(71) Applicant: Covidien LP, Mansfield, MA (US)

(72) Inventors: Jeevan Maddur Shankarsetty, Bangalore (IN); Hari Naga Mahesh Kalepu, Hyderabad (IN)

(73) Assignee: Covidien LP, Mansfield, MA (US)

( * ) Notice: Subject to any disclaimer, the term of this patent is extended or adjusted under 35 U.S.C. 154(b) by 137 days.

This patent is subject to a terminal disclaimer.

(21) Appl. No.: 17/183,759

(22) Filed: Feb. 24, 2021

(65) Prior Publication Data

US 2021/0177409 A1 Jun. 17, 2021

Related U.S. Application Data

(63) Continuation of application No. 15/826,837, filed on Nov. 30, 2017, now Pat. No. 10,939,910.

(30) Foreign Application Priority Data

Dec. 2, 2016 (IN) .............................. 201611041364

(51) Int. Cl.
*A61B 17/072* (2006.01)
*A61B 90/00* (2016.01)
*A61B 17/00* (2006.01)

(52) U.S. Cl.
CPC ............ *A61B 17/072* (2013.01); *A61B 90/03* (2016.02); *A61B 2017/00407* (2013.01);
(Continued)

(58) Field of Classification Search
CPC .............. A61B 17/115; A61B 17/3211; A61B 17/3476; A61B 90/98; A61B 2034/252;
(Continued)

(56) References Cited

U.S. PATENT DOCUMENTS 1,158,111 A 10/1915 Ahlheim
2,891,250 A 6/1959 Hirata
(Continued)

FOREIGN PATENT DOCUMENTS

EP 2484292 A1 8/2012
WO 2014043971 A1 3/2014
(Continued)

OTHER PUBLICATIONS

European Search Report dated Apr. 24, 2018 in EP Appln. No. 17204912.
(Continued)

*Primary Examiner* — Joshua G Kotis
*Assistant Examiner* — Scott A Howell
(74) *Attorney, Agent, or Firm* — Carter, DeLuca & Farrell LLP

(57) ABSTRACT

The present disclosure relates to a surgical stapling instrument comprising a handle assembly, an elongated body portion extending from the handle assembly, and an end effector supported on a distal portion of the elongated body portion. The end effector includes a curved housing having a base portion and a jaw portion, a curved anvil assembly supported on the jaw portion, and a curved cartridge assembly supported on the base portion. The cartridge assembly defining first and second arrays of staples receiving slots, the first array of staple receiving slots includes three rows of staples and the second array of staple receiving slots includes two rows of staples. A height of the staples in each of the rows of three rows of staples of the first array of staple receiving slots is different.

10 Claims, 14 Drawing Sheets

(52) U.S. Cl.
CPC ........... *A61B 2017/00477* (2013.01); *A61B 2017/07221* (2013.01); *A61B 2017/07228* (2013.01); *A61B 2017/07242* (2013.01); *A61B 2017/07264* (2013.01); *A61B 2017/07271* (2013.01); *A61B 2017/07285* (2013.01); *A61B 2090/034* (2016.02); *A61B 2090/036* (2016.02); *A61B 2090/0811* (2016.02); *A61B 2090/0814* (2016.02)

(58) Field of Classification Search
CPC ........ A61B 2217/007; A61B 2090/038; A61B 2090/064; A61B 2090/0803; A61B 2090/0808; A61B 2090/0811; A61B 2090/0814; A61B 2017/00017; A61B 2017/00022; A61B 2017/00115; A61B 2017/00119; A61B 2017/00367; A61B 2017/00398; A61B 2017/0046; A61B 2017/00473; A61B 2017/00477; A61B 2017/00725; A61B 2017/00734; A61B 2017/00818; A61B 2017/2903
See application file for complete search history.

(56) References Cited

U.S. PATENT DOCUMENTS

| | | |
|---|---|---|
| 3,080,564 A | 3/1963 | Strekopov et al. |
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,319,576 A | 3/1982 | Rothfuss |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,397,324 A | 3/1995 | Carroll et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,474,223 A | 12/1995 | Viola et al. |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 * | 10/2004 | Bilotti ............... A61B 17/115 227/176.1 |
| 6,817,508 B1 | 11/2004 | Racenet et al. |

(56) References Cited

U.S. PATENT DOCUMENTS

| | | |
|---|---|---|
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,237,708 B1 | 7/2007 | Guy et al. |
| 7,275,674 B2 | 10/2007 | Racenet et al. |
| RE40,237 E | 4/2008 | Bilotti et al. |
| 7,407,075 B2 * | 8/2008 | Holsten .......... A61B 17/11 227/19 |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,717,312 B2 | 5/2010 | Beetel |
| 7,731,073 B2 | 6/2010 | Wixey et al. |
| 7,735,704 B2 | 6/2010 | Bilotti |
| 7,766,207 B2 | 8/2010 | Mather et al. |
| 7,810,690 B2 | 10/2010 | Bilotti et al. |
| 7,886,953 B2 | 2/2011 | Schwemberger et al. |
| 3,016,176 A1 | 9/2011 | Kasvikis et al. |
| 3,029,520 A1 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,360,296 B2 | 1/2013 | Zingman |
| 8,424,738 B2 | 4/2013 | Kasvikis |
| 8,499,994 B2 | 8/2013 | D'Arcangelo |
| 8,523,042 B2 | 9/2013 | Masiakos et al. |
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 | 9/2015 | Mandakolathur Vasudevan et al. |
| 9,192,382 B2 | 11/2015 | Kostrzewski |
| 9,839,420 B2 | 12/2017 | Shelton, IV |
| 9,872,683 B2 | 1/2018 | Hopkins |
| 9,993,245 B2 | 6/2018 | Levy |
| 10,939,910 B2 | 3/2021 | Maddur Shankarsetty et al. |
| 2004/0164123 A1 | 8/2004 | Racenet et al. |
| 2005/0139634 A1 * | 6/2005 | Schwemberger .... A61B 17/072 227/19 |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2007/0034666 A1 * | 2/2007 | Holsten .......... A61B 17/115 227/176.1 |
| 2007/0034667 A1 * | 2/2007 | Holsten .......... A61B 17/072 227/176.1 |
| 2007/0187456 A1 | 8/2007 | Viola et al. |
| 2010/0048988 A1 | 2/2010 | Pastorelli et al. |
| 2012/0080498 A1 * | 4/2012 | Shelton, IV ....... A61B 17/072 227/180.1 |
| 2013/0206813 A1 | 8/2013 | Nalagatla |
| 2013/0248578 A1 | 9/2013 | Arteaga Gonzalez |
| 2016/0249914 A1 | 9/2016 | Zhang et al. |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0055991 A1 * | 3/2017 | Kang .............. A61B 17/072 |

FOREIGN PATENT DOCUMENTS

| | | |
|---|---|---|
| WO | 2015153340 A2 | 10/2015 |
| WO | 2016171395 A1 | 10/2016 |
| WO | 2017173025 A2 | 10/2017 |

OTHER PUBLICATIONS

European Search Report dated Jul. 27, 2018 in EP Appln. No. 17204912.

* cited by examiner

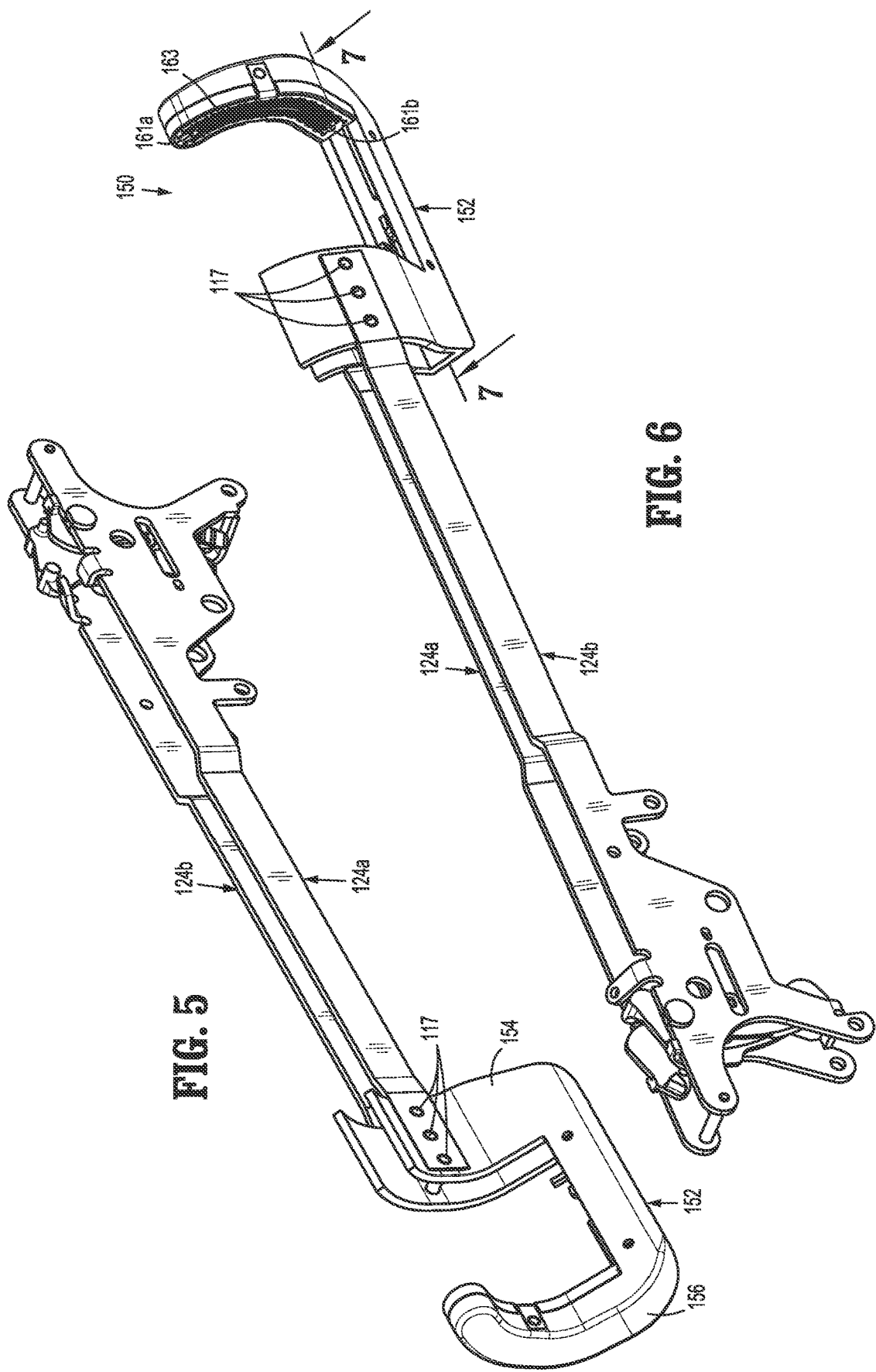

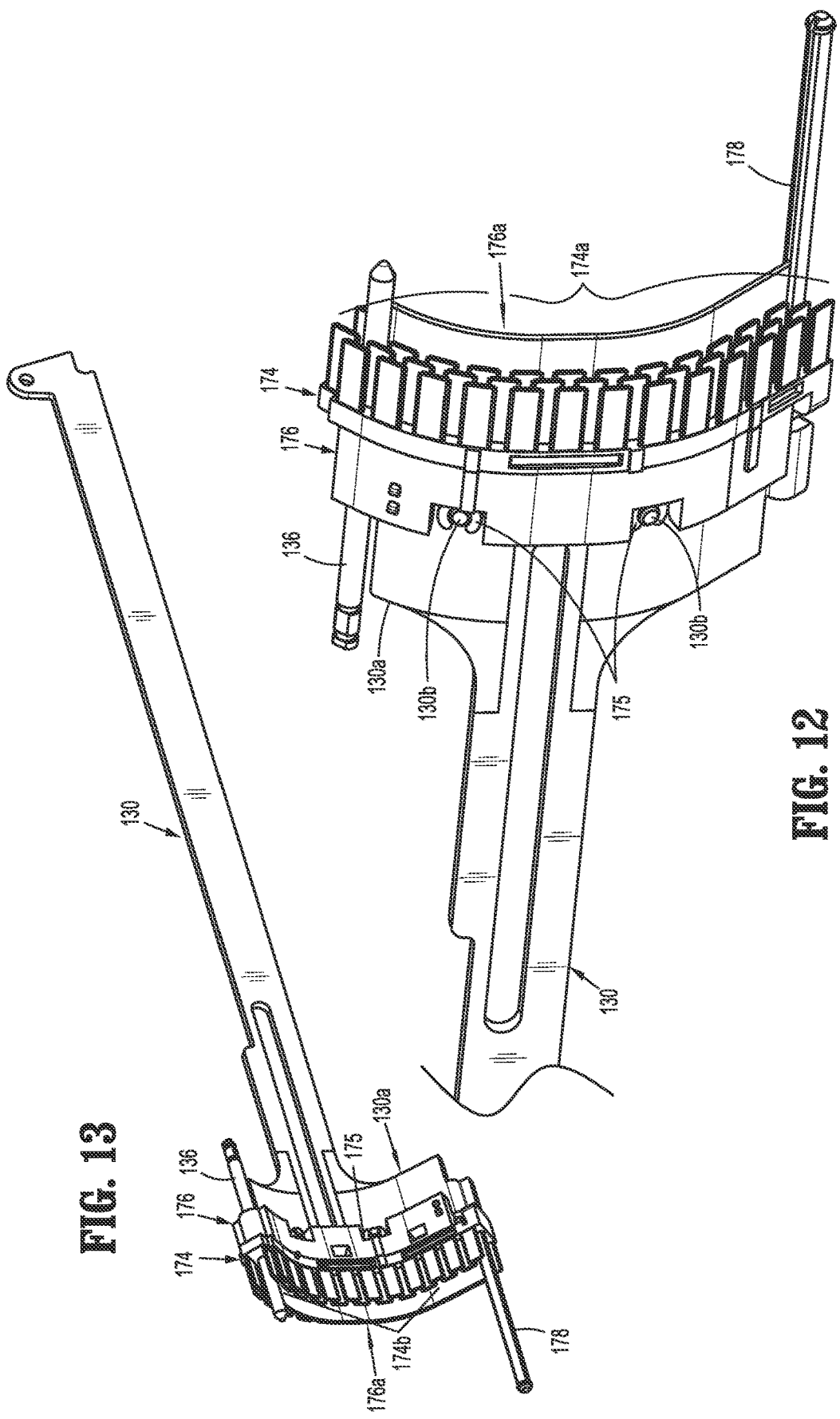

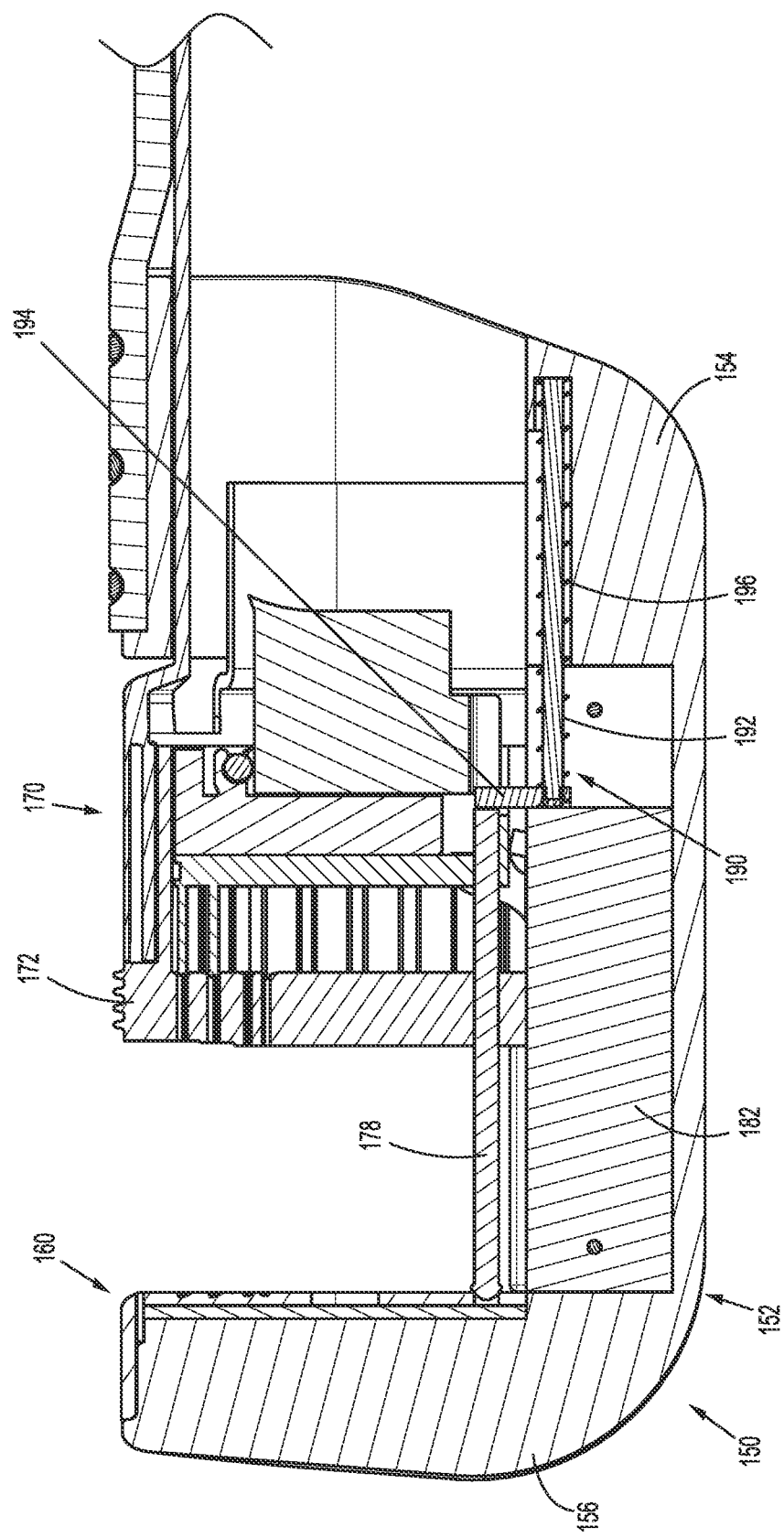

SURGICAL STAPLING INSTRUMENT WITH CURVED END EFFECTOR

CROSS REFERENCE TO RELATED APPLICATION

This application is a continuation of U.S. patent application Ser. No. 15/826,837, filed Nov. 30, 2017, which claims the benefit of and priority to Indian Application Serial No. 201611041364, filed on Dec. 2, 2016 the entire contents of which are incorporated herein by reference in their entireties.

BACKGROUND

Technical Field

The present disclosure relates generally to a surgical instrument and, more specifically, to a surgical stapling instrument for clamping, and joining and/or cutting tissue.

Background of Related Art

Certain surgical stapling instruments are used for applying rows of staples through compressed living tissue. These surgical stapling instruments are employed, for example, for fastening tissue or organs prior to transection or resection or during anastomoses. In some cases, these surgical stapling instruments are utilized for occluding organs in thoracic and abdominal procedures.

Typically, such surgical stapling instruments include an anvil assembly, a cartridge assembly for supporting an array of surgical staples, an approximation mechanism for approximating the cartridge and anvil assemblies, an alignment or guide pin assembly for capturing tissue between the cartridge and anvil assemblies and/or for maintaining alignment between the cartridge and anvil assemblies during approximation and firing, and a firing mechanism for ejecting the surgical staples from the cartridge assembly.

In use, a surgeon initially advances the alignment pin assembly and subsequently approximates the anvil and cartridge assemblies. In some surgical stapling instruments, the alignment pin is automatically advanced in response to approximation of the anvil and cartridge assemblies. Next, the surgeon fires the surgical stapling instrument to place staples in tissue. Optionally, the surgeon may use the same surgical stapling instrument or a separate device to cut tissue positioned adjacent or between the rows of staples. In some instances, the surgical stapling instrument includes a knife which cuts tissue as the staples are fired.

In certain procedures, it may be difficult to access the target organ or tissue for resection and application of rows of staples. It would be advantageous to provide a surgical stapling instrument that is configured to improve access to hard to reach areas, and one having improved maneuverability.

SUMMARY

The present disclosure relates to a surgical stapling instrument comprising a handle assembly, an elongated body portion extending from the handle assembly and defining a longitudinal axis, and an end effector supported on a distal portion of the elongated body portion. The end effector includes a curved housing having a base portion and a jaw portion, a curved anvil assembly supported on the jaw portion, and a curved cartridge assembly supported on the base portion. The cartridge assembly defining first and second arrays of staples receiving slots. The first array of staple receiving slots includes three rows of staples and the second array of staple receiving slots includes two rows of staples. A height of the staples in each of the rows of three rows of staples of the first array of staple receiving slots is different. The base portion is secured to the distal portion of the elongated body portion.

In embodiments, the cartridge assembly includes a staple cartridge and a tissue guard extendable from the staple cartridge. The end effector may include a tissue guard assembly configured to advance the tissue guard into contact with the anvil assembly when the cartridge assembly is secured to the housing of the end effector.

The surgical stapling instrument of the present disclosure may further include an indicator feature on the elongated body portion for indicating to a clinician the position of the cartridge assembly relative to the anvil assembly. An indicator feature may instead, or additionally, be formed on the housing of the end effector. Embodiments of the surgical stapling instrument include an indicator mechanism disposed within the handle assembly for indicating to a clinician the position of the cartridge assembly relative to the anvil assembly. The indicator mechanism may be a wheel member rotatably supported within the handle assembly. The wheel member may include first, second and third marks configured to indicate the position of the cartridge assembly in relation to the anvil assembly.

In embodiments, the cartridge assembly defines a knife receiving slot between the first array of staple receiving slots and the second array of staple receiving slots. The first array of staple receiving slots may be disposed radially outwardly of the knife receiving slot. A height of the staples in a row of the first array of staple receiving slots closest to the knife receiving slot may be shorter than a height of the staples in a row of the first array of stapling receiving slots furthest from the knife receiving slot.

BRIEF DESCRIPTION OF THE DRAWINGS

Various embodiments of the presently disclosed surgical stapling instrument are disclosed herein with reference to the drawings, wherein:

FIGS. 5 and 6 are perspective views from opposite sides of a frame member and an end effector of the surgical stapling instrument shown in FIGS. 1 and 2;

FIG. 12 is a perspective view of a distal end of a thrust bar, a knife, a knife pusher, an alignment pin, and a staple pusher member of the surgical stapling instrument shown in FIGS. 1 and 2;

FIG. 13 is a perspective view of the thrust bar, the knife, the knife pusher, the alignment pin, and the staple pusher member shown in FIG. 12;

FIG. 14 is a cross-sectional side view of the end effector of the surgical stapling instrument shown in FIGS. 1 and 2, showing a tissue guard of the cartridge assembly in an advanced position;

DETAILED DESCRIPTION OF THE EMBODIMENTS

Figure 1:
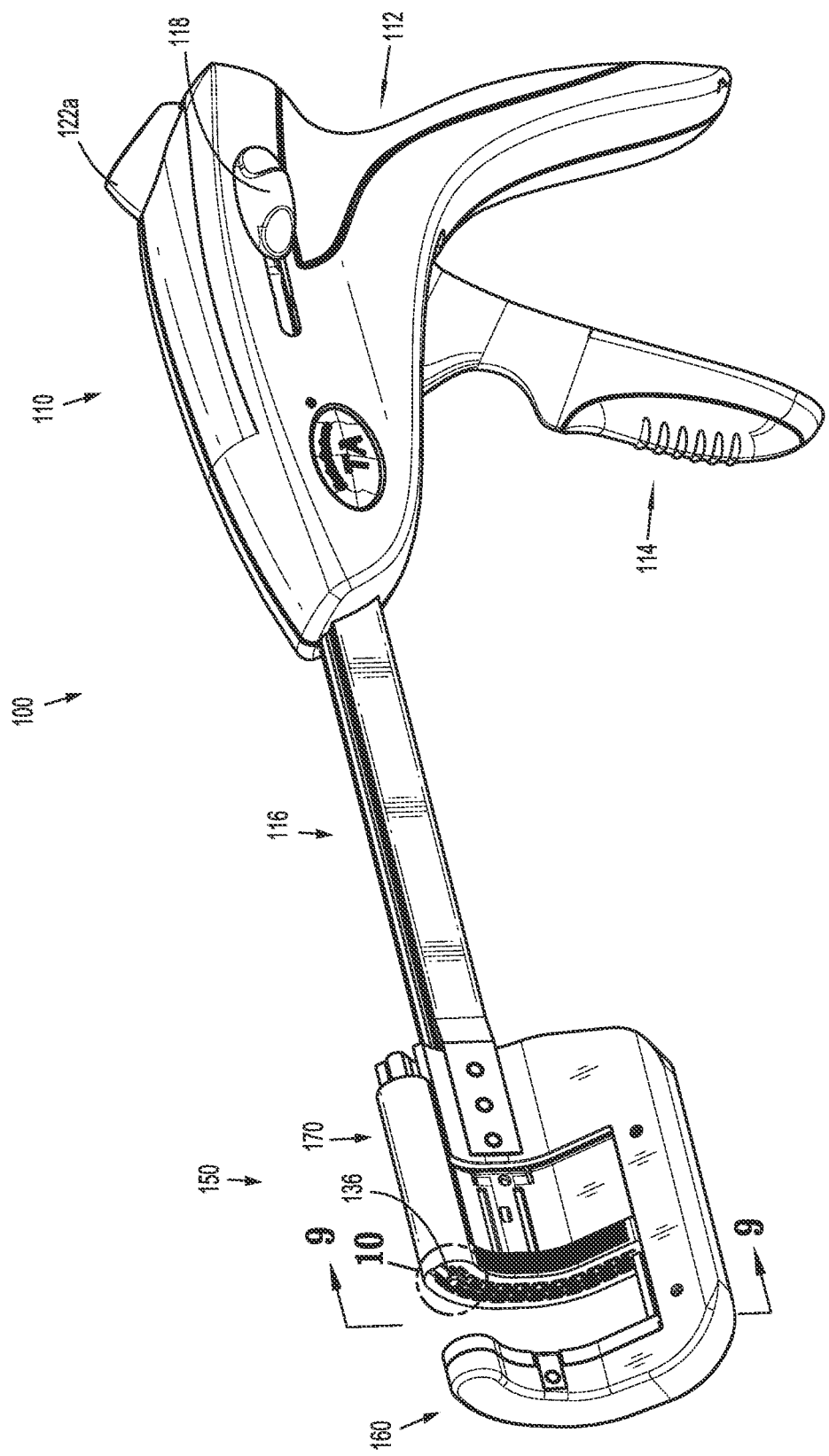
FIGS. 1 and 2 are perspective views from opposite sides of a surgical stapling instrument according to an embodiment of the present disclosure with the end effector in an open position.

Embodiments of the presently disclosed surgical stapling instrument are described in detail with reference to the drawings, wherein like reference numerals designate corresponding elements in each of the several views. In the drawings and the description that follows, the term "proximal" refers to the end of the surgical stapling instrument that is closer to the clinician, whereas the term "distal" refers to the end of the surgical stapling instrument that is farther from the clinician. In addition, the term clinician is used generally to refer to medical personnel including doctors, nurses, and support personnel.

It should be appreciated that the instrument described and illustrated herein is configured to fire surgical staples against an anvil surface; however, aspects of the present disclosure are equally applicable with other forms of staples, fasteners, clips, as well as two part fasteners, made of metallic or polymeric material.

Embodiments of the presently disclosed surgical stapling instruments include a curved end effector having a curved anvil assembly and a curved cartridge assembly. The curved configuration of the end effector improves the capability of the instrument to access surgical sites within a patient, and improves the ability of the instrument to clamp and/or to join particular tissue within the body during surgical procedures. The curved end effector may also improve visualization of a surgical site and allow more room for a clinician to manipulate tissue or the end effector within the body. Additionally, the curved end effector may increase the effective tissue cutting length (as measured along a knife slot) as compared to a linear end effector. In embodiments, the surgical stapling instruments include an indicator for providing the clinician with an indication of the position of the cartridge assembly of the surgical stapling instrument, e.g., open, partially clamped, clamped.

Figure 2:
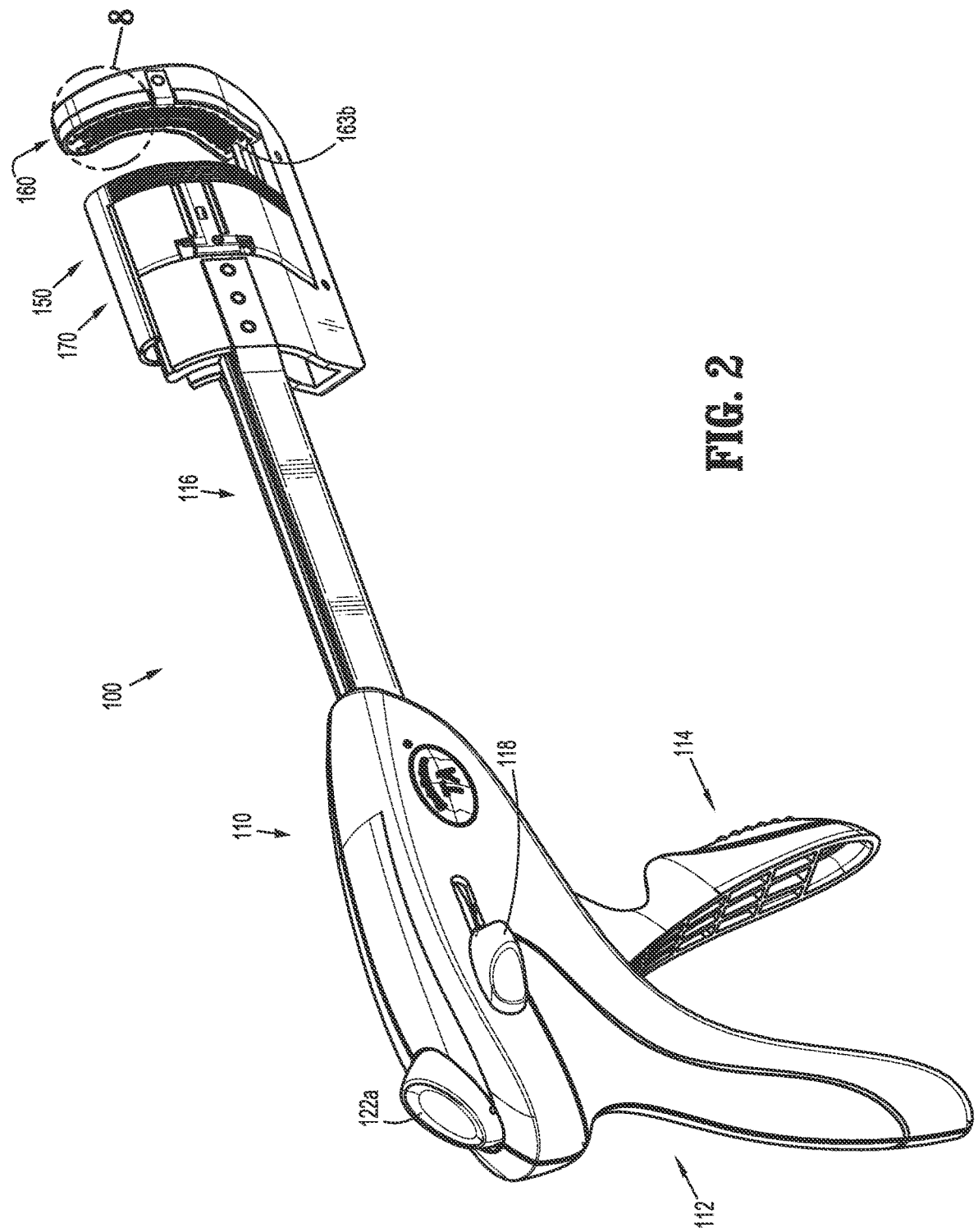

With reference now to FIGS. 1 and 2, a surgical stapling instrument according to an embodiment of the present disclosure is shown generally as surgical stapling instrument 100. The surgical stapling instrument 100 includes a handle assembly 110 having a stationary handle or base 112, a trigger member 114 pivotally secured relative to the stationary handle 112, and an elongated body portion 116 extending distally from the stationary handle 112. An end effector 150 is secured to a distal portion of the elongated body portion 116 and includes a cartridge assembly 160 and an anvil assembly 170. A thumb button 118 is slidably positioned on each side of the stationary handle 112 of the handle assembly 110. The thumb buttons 118 are movable to manually advance an alignment pin 136. A release button 122a of a release mechanism 120 (FIG. 3) is positioned on the proximal portion of the stationary handle 112 and is depressible to allow the cartridge assembly 170 to automatically return from a fully approximated or clamped position, disposed adjacent to the anvil assembly 160 (see, for example, FIG. 20), to an open position, spaced from the anvil assembly 160 (see, for example, FIG. 18).

The structure and function of the handle assembly 110 of the surgical stapling instrument 100 will only be described to the extent necessary to fully disclose particular aspects of the present disclosure. For a detailed description of an exemplary handle assembly, please refer to commonly owned U.S. Pat. No. 6,817,508 ("the '508 patent"), the content of which is hereby incorporated by reference herein in its entirety.

Figure 3:
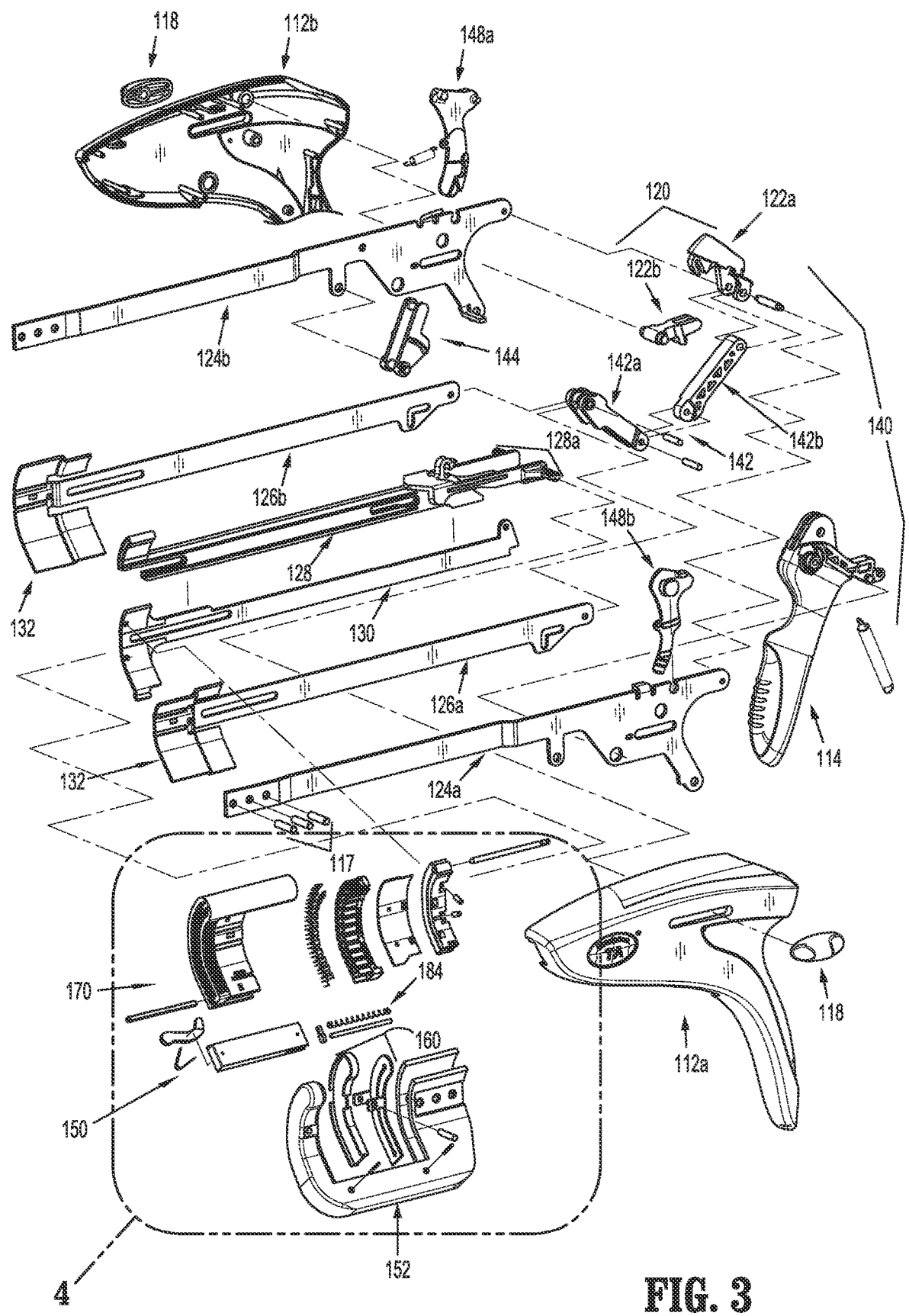
FIG. 3 is a perspective, assembly view of the surgical stapling instrument shown in FIGS. 1 and 2.

With reference also to FIG. 3, the stationary handle 112 of the handle assembly 110 of the surgical stapling instrument 100 is formed from a pair of half-sections 112a, 112b. A pair of spaced frame members 124a, 124b extends between the half-sections 112a, 112b and a housing 152 of the end effector 150. A pair of clamp slide members 126a, 126b, an alignment pin pusher 128, and a thrust bar 130 are slidably supported between the frame members 124a, 124b for movement between retracted and advanced positions in response to movement of the trigger member 114 through an approximation stroke and/or a firing stroke, as described in the '508 patent.

The clamp slide members 126a, 126b form part of an approximation mechanism of the surgical stapling instrument 100. As will be described in further detail below, a distal portion of each clamp slide member 126a, 126b includes a head portion 132. The head portions 132 are configured to releasable support the cartridge assembly 170 of the end effector 150.

The alignment pin pusher 128 and thrust bar 130 are slidably disposed between the clamp slide members 126a, 126b. The alignment pin pusher 128 slidably receives the thrust bar 130 and is configured to engage an alignment pin 136 such that when the alignment pin pusher 128 is moved to an advanced position, the alignment pin 136 is advanced from within cartridge assembly 170 into an opening 163a (FIG. 8) of the anvil assembly 160. The thumb buttons 118 are fastened to posts 128a of the alignment pin pusher 128 to facilitate manual actuation of the alignment pin pusher 128. The thrust bar 130 is slidably positioned within an elongated slot (not shown) defined within the alignment pin pusher 128 and includes an engagement head 128a configured to engage a knife pusher 176 of the cartridge assembly 170.

An actuation assembly 140 is operably disposed within the stationary handle 112 of the handle assembly 110 of the surgical stapling instrument 100 and includes a bi-linkage assembly 142 having a front link 142a and a rear link 142b, a bell crank 144, a clamping pawl 146a, and a firing pawl 146b. The release mechanism 120 is operably connected to the actuation assembly 140 and includes the release button 122a and a release lever 122b. Through actuation of the trigger member 114, the actuation assembly 140 operates to individually advance the clamp slide members 126a, 126b to move the cartridge assembly 170 towards the clamped position (see, for example, FIG. 20), and advance the thrust bar 130, to eject staples "S" from the cartridge assembly 170. The release mechanism 120 operates to permit return of the cartridge assembly 170 to an open position.

For a detailed description of the structure and function of an exemplary handle actuation assembly and an exemplary release mechanism, please refer to the '508 patent, the content of which was previously incorporated by reference.

Figure 4:
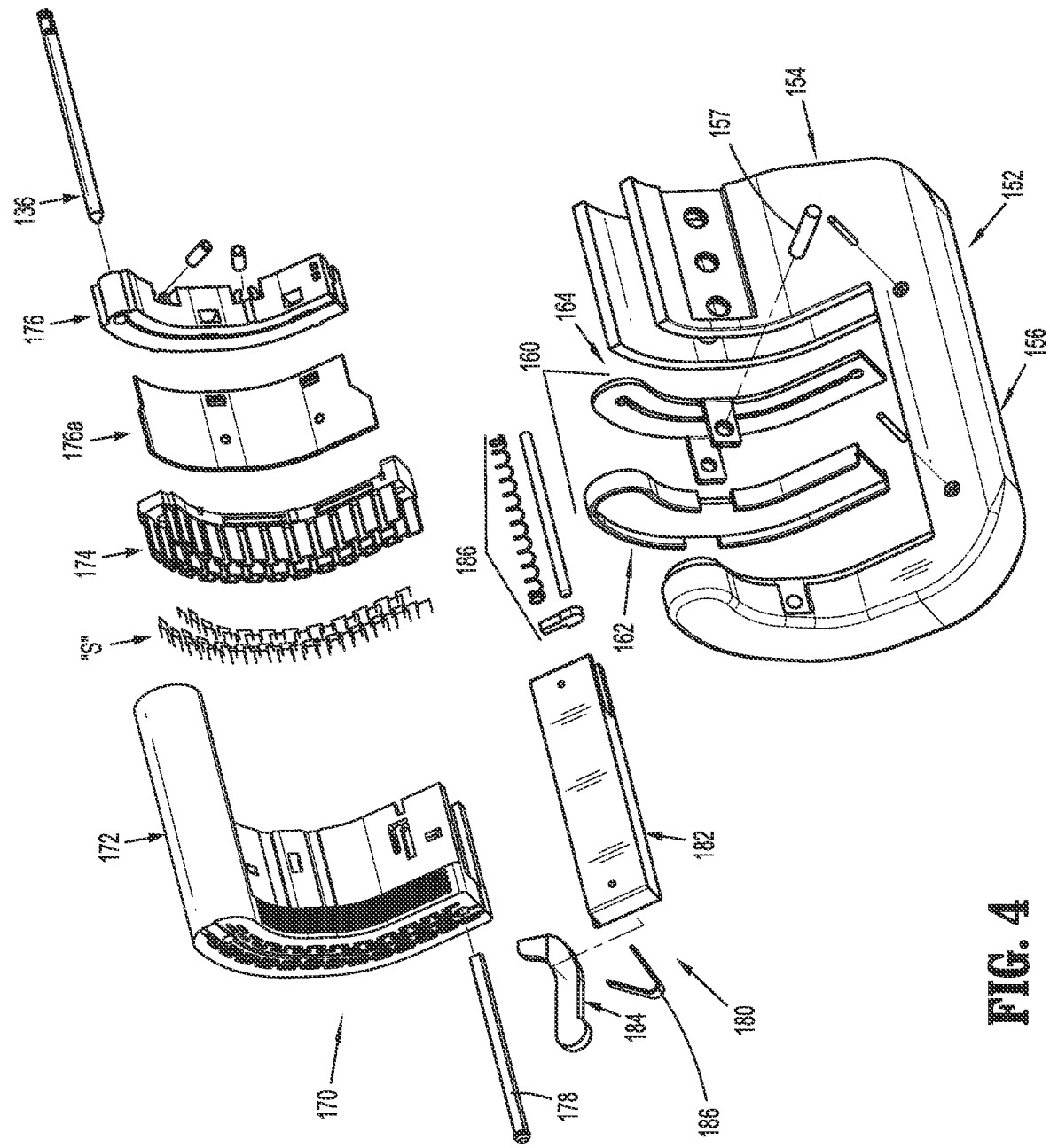
FIG. 4 is an enlarged view of the area of detail indicated in FIG. 3.

With reference to FIGS. 4-6, the end effector 150 of the surgical stapling instrument 100 (FIG. 1) includes a housing 152 having a base portion 154 and an L-shaped jaw portion 156 extending from the base portion 154. Although shown secured to the distal portion of the elongated body portion 116 of the handle assembly 110 by rivets 117 (FIGS. 5 and 6), it is envisioned that the housing 152 of the end effector 150 may be secured to a distal portion of the body portion 116 of the handle assembly 110 in any suitable manner, e.g., welding, mechanical fasteners. The anvil assembly 160 is supported on the jaw portion 156 of the housing 152 and the cartridge assembly 170 is releasably supported within the base portion 154 of the housing 152.

The housing 152 of the end effector 150 includes a substantially curved, C-like, or hook shaped cross-section. In embodiments, and as shown, the end effector 150 includes a first radius of curvature and a second radius of curvature. The first and second radii of curvature may be increased or decreased to suit a particular procedure and/or to accommodate a particular patient. In embodiments, the curvature of the end effector 150 is formed by substantially linear sections of the end effector 150. As will be described in detail below, each of the anvil assembly 160 and the cartridge assembly 170 include a curved configuration corresponding to the curved configuration of the housing 152 of the end effector 150.

As noted above, the curved configuration of the end effector 150 improves the capability of the instrument to access surgical sites within a patient, and improves the ability of the instrument to clamp and/or to join particular tissue within the body during surgical procedures. The curved end effector 150 may also improve visualization of a surgical site and allow more room for a clinician to manipulate tissue or an end effector of the instrument within the body. Additionally, the curved end effector 150 may increase the effective tissue cutting length (as measured along a knife slot) as compared to a linear end effector.

Figure 7:
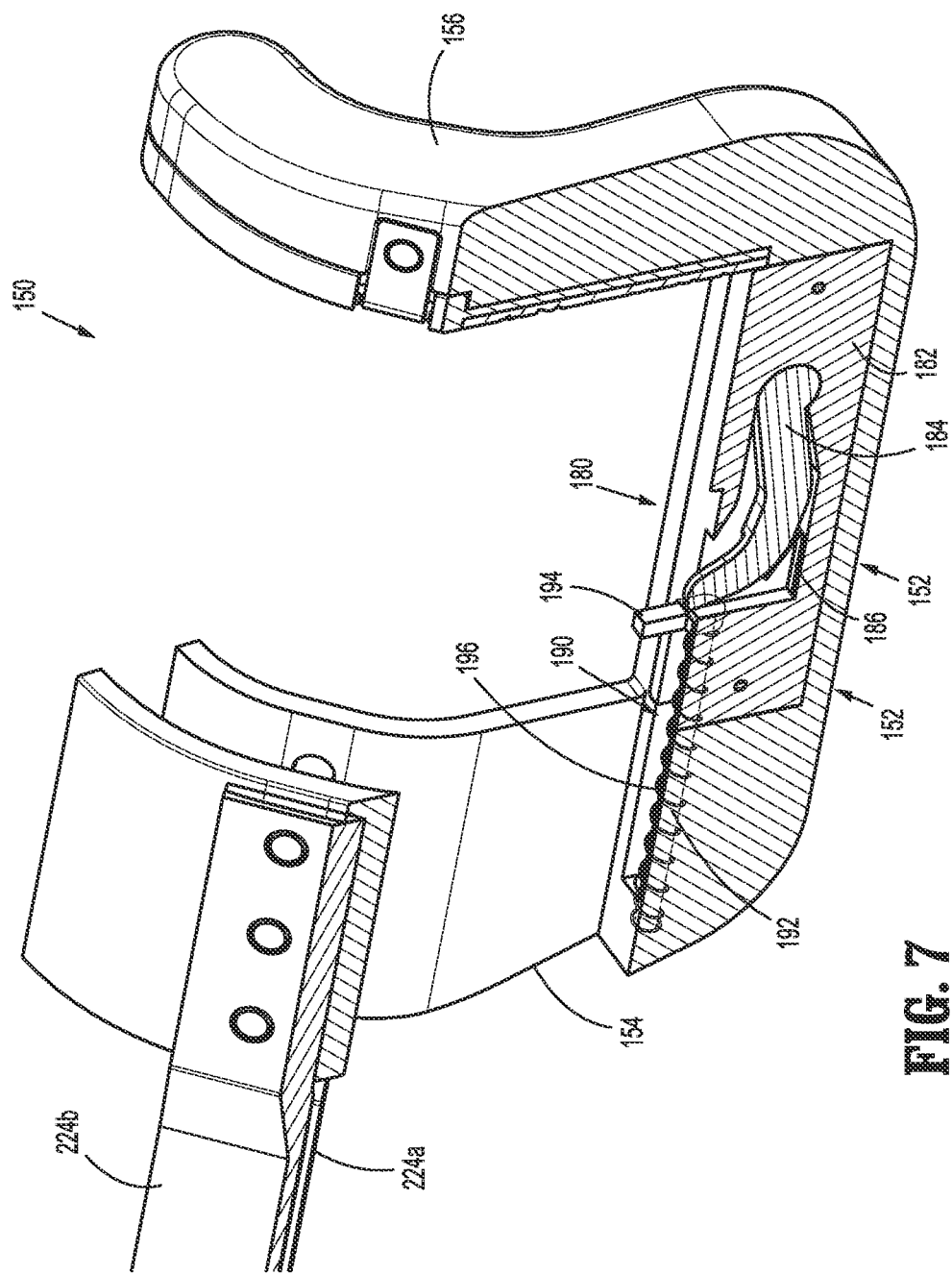
FIG. 7 is a cross-sectional side view taken along line 7-7 shown in FIG. 6.

With particular reference to FIG. 7, the jaw portion 156 of the housing 152 of the end effector 150 supports an interlock assembly 180. The interlock assembly 180 prevents firing of the surgical stapling instrument 100 with a spent cartridge assembly, i.e., a cartridge assembly in which the staples "S" have already been fired, until new cartridge assembly (not shown) is replaced. The interlock assembly 180 includes a holder 182, a lock member 184 pivotally received within the holder 182, and a spring 186 biasing the lock member 184 to an extended position (not shown). The interlock assembly 180 prevents readvancement of the thrust bar 130 of the handle assembly 110 when a spent cartridge assembly 170 is supported within the housing 152 of the end effector 150. For a detailed description of the structure and function of an exemplary interlock assembly, please refer to the '508 patent.

The jaw portion 156 of the housing 152 of the end effector 150 also supports a tissue guard assembly 190 for advancing a tissue guard 178 from the cartridge assembly 170 to prevent over insertion of tissue between the anvil assembly 160 and the cartridge assembly 170, e.g., to prevent tissue from extending below the staple line of the cartridge assembly 170. The tissue guard assembly 190 includes a pusher pin 192, a pusher member 194 mounted on a distal portion of the pusher pin 192, and a spring 196 received about the pusher pin 192 for biasing the pusher pin 192 distally. Although shown as separate components, it is envisioned that the pusher pin 192 and the pusher member 194 may be integrally formed, e.g., monolithic. As will be described in further detail below, the pusher pin 192 is maintained in a retracted position by the lock member 184 of the interlock assembly 180. Loading of a cartridge assembly 170 within the housing 152 of the end effector 150 depresses the lock member 184, thereby releasing the pusher pin 192. The pusher member 194 on the pusher pin 192 engages the tissue guard 178, causing advancement of the tissue guard 178 into engagement with the anvil assembly 160.

With reference back to FIG. 4, the anvil assembly 160 of the end effector 150 includes a base plate 162 and an anvil member 164. The base plate 162 and anvil member 164 define the same curved profile as the jaw portion 156 of the housing 152 of the end effector 150. In embodiments, the anvil member 164 is secured to the jaw portion 154 of the housing 152 by a rivet 157. The base plate 162 is supported on the jaw portion 156 and is received between the jaw portion 156 and the anvil member 164. The base plate 162 is clamped to the jaw portion 154 of the housing 152 by the anvil member 164.

Figure 8:
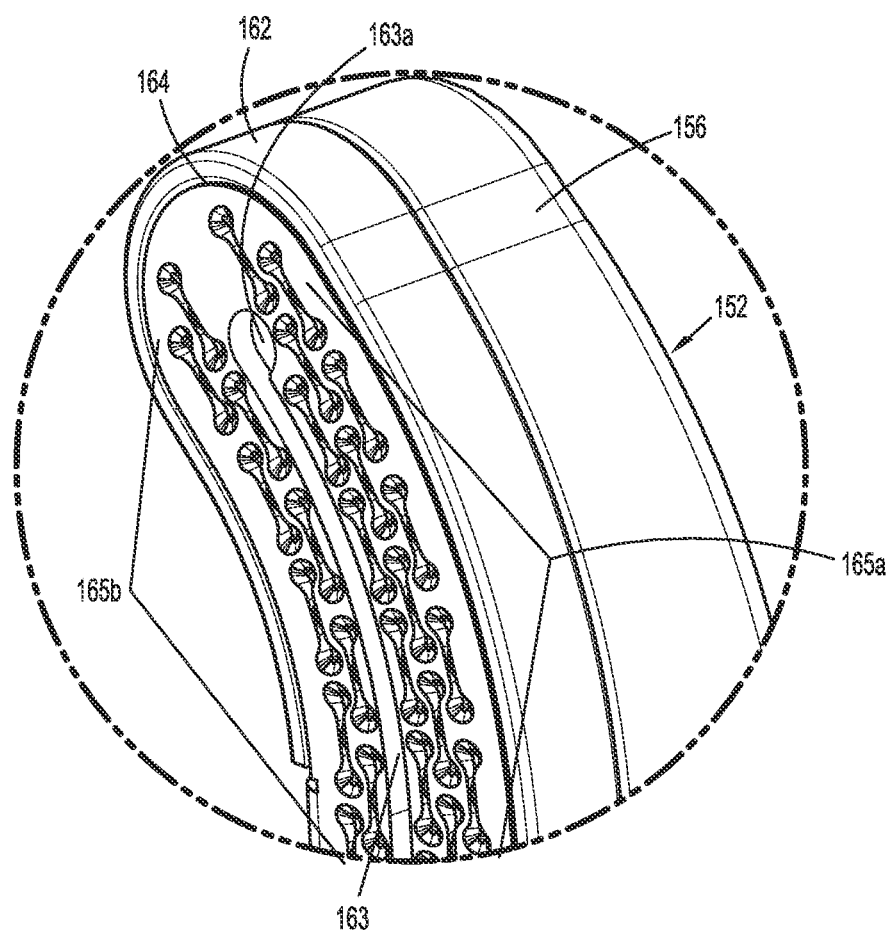
FIG. 8 is an enlarged view of the area of detail indicated in FIG. 2.

With particular reference to FIG. 8, the anvil member 164 defines a longitudinal slot 163 configured for receipt of a knife member 176a (FIG. 4) of the cartridge assembly 170 (FIG. 4). A first opening 163a is formed on a first portion of the longitudinal slot 163 and is configured to receive a distal portion of the alignment pin 136 (FIG. 4). A second opening 163b (FIG. 2) is formed on a second portion of the longitudinal slot 163 and is configured to receive a distal portion of a tissue guard 178 (FIG. 4).

The anvil member 164 defines first and second sets of staple pockets 165a, 165b formed in the surface of the anvil member 164. The position of the first and second sets of staple pockets 165a, 165b correspond to the position of the first and second arrays of staple receiving slots 171a, 171b, respectively, of a staple cartridge 172 of the cartridge assembly 170. As will be described in further detail below with regards to the cartridge assembly 170, the anvil member 164 includes three rows of pockets in the first set of staple pockets 165a formed on a first or radial outward side of the longitudinal slot 163, and two rows of pockets in the second set of staple pockets 165b formed on a second or radially inward side of the longitudinal slot 163.

With reference again to FIG. 4, the cartridge assembly 170 of the end effector 150 of the surgical stapling instrument 100 (FIG. 1) includes the staple cartridge 172 including the same curved profile as the base portion 156 of the housing 152 of the end effector 152. As described above with regards to the housing 152 of the end effector 150, in embodiments, the staple cartridge 172 includes first and second radii of curvature. As also described above with regards to the housing 152, the curvature of the staple cartridge 172 may be formed by substantially linear sections of the staple cartridge 172. In embodiments, a distal portion of the staple cartridge 172 may be curved in substantially hook-like manner to assist in manipulation of tissue.

The staple cartridge 172 defines first and second arrays of staple receiving slots 171a, 171b for receiving staples "S", a knife receiving slot 173, a first opening 173a formed on a first portion of the knife receiving slot 173 configured to receive the alignment pin 136, and a second opening 173b formed on a second portion of the knife receiving slot 163 configured to receive the tissue guard 178. In embodiments, the first array of staple receiving slots 171a is formed radially outwardly of the knife receiving slot 173 and includes three rows of slots, while the second array of staple receiving slots 171b is formed radially inwardly of the knife receiving slot 171 and includes two rows of slots. Other configurations of the staple receiving slots 171a are envisioned.

Figure 10:
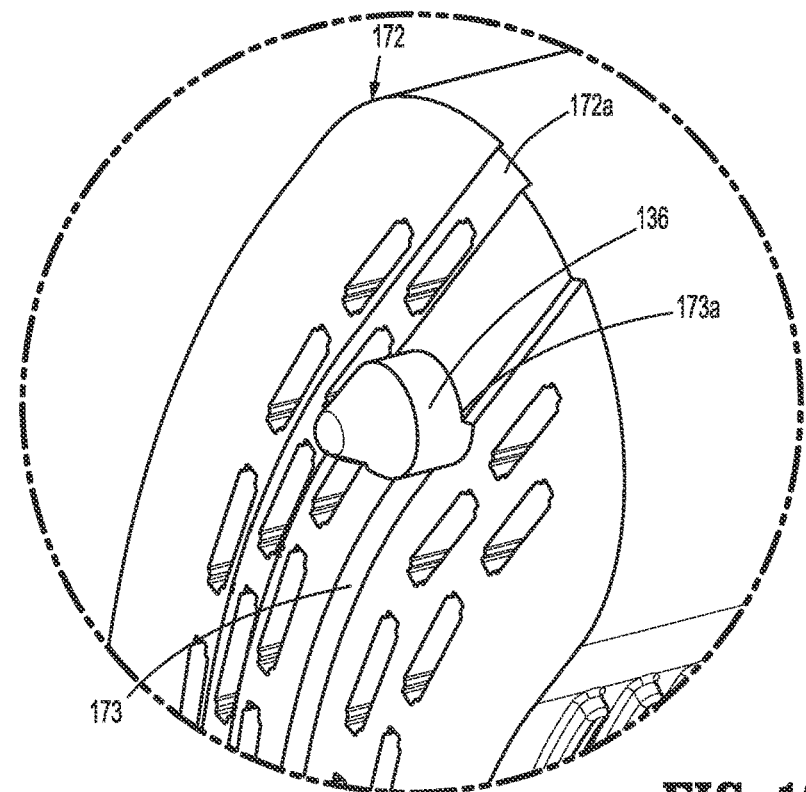
FIG. 10 is an enlarged view of the area of detail indicated in FIG. 1.
Figure 9:
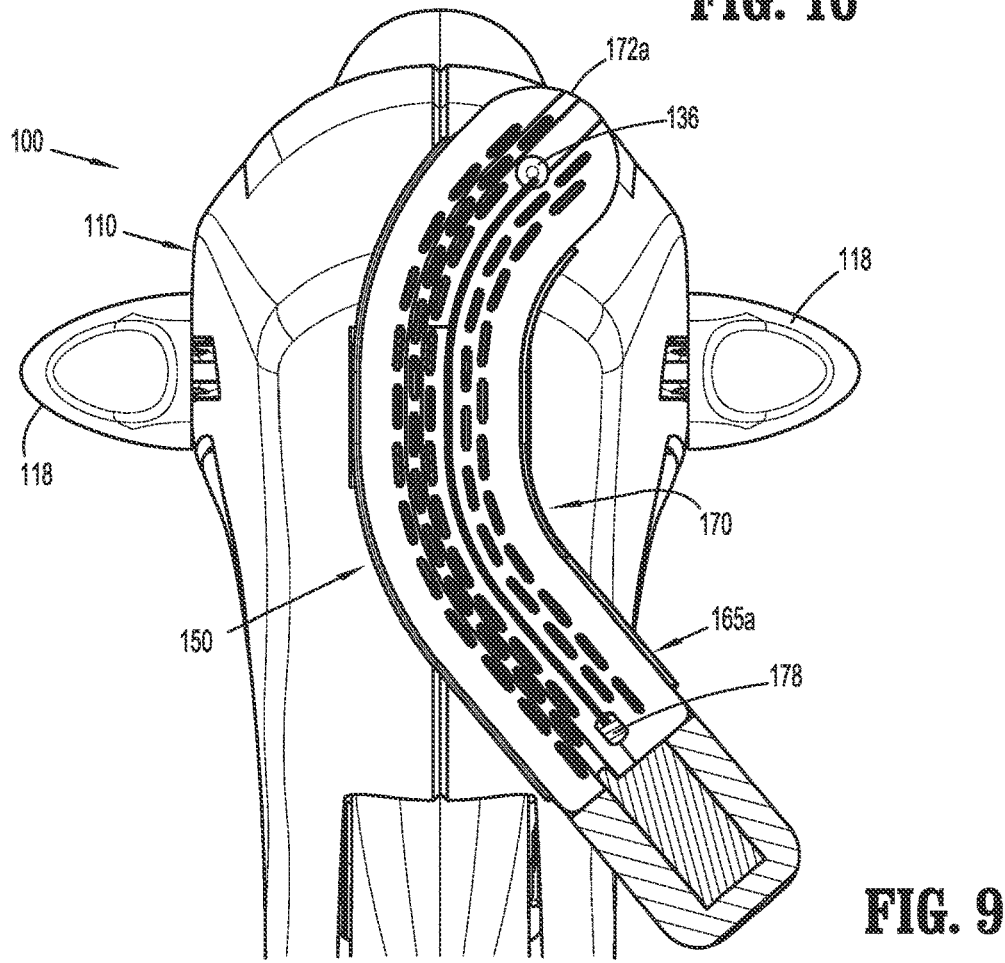
FIG. 9 is a cross-sectional side view taken along line 9-9 shown in FIG. 1.

As shown in FIGS. 9 and 10, in embodiments, the staple cartridge 172 includes a stepped tissue contacting surface 172a. In embodiments, and as shown, the staples "S" (FIG. 3) in each row of the first array of staple receiving slots 171a have a height different from the staples "S" in an adjacent row of the first array of staple receiving slots 171a. As shown, the height of the staples "S" in each of the rows of the first array of staple receiving slots 171a increase in height the further the row is from the knife receiving slot 173. This stepped configuration is described in detail in commonly owned U.S. Pat. No. 7,407,075, the content of which is incorporated herein by reference in its entirety. Although shown including the stepped configuration, it is envisioned that embodiments of the cartridge assembly may include alternative numbers and/or configurations of staples.

Figure 11:
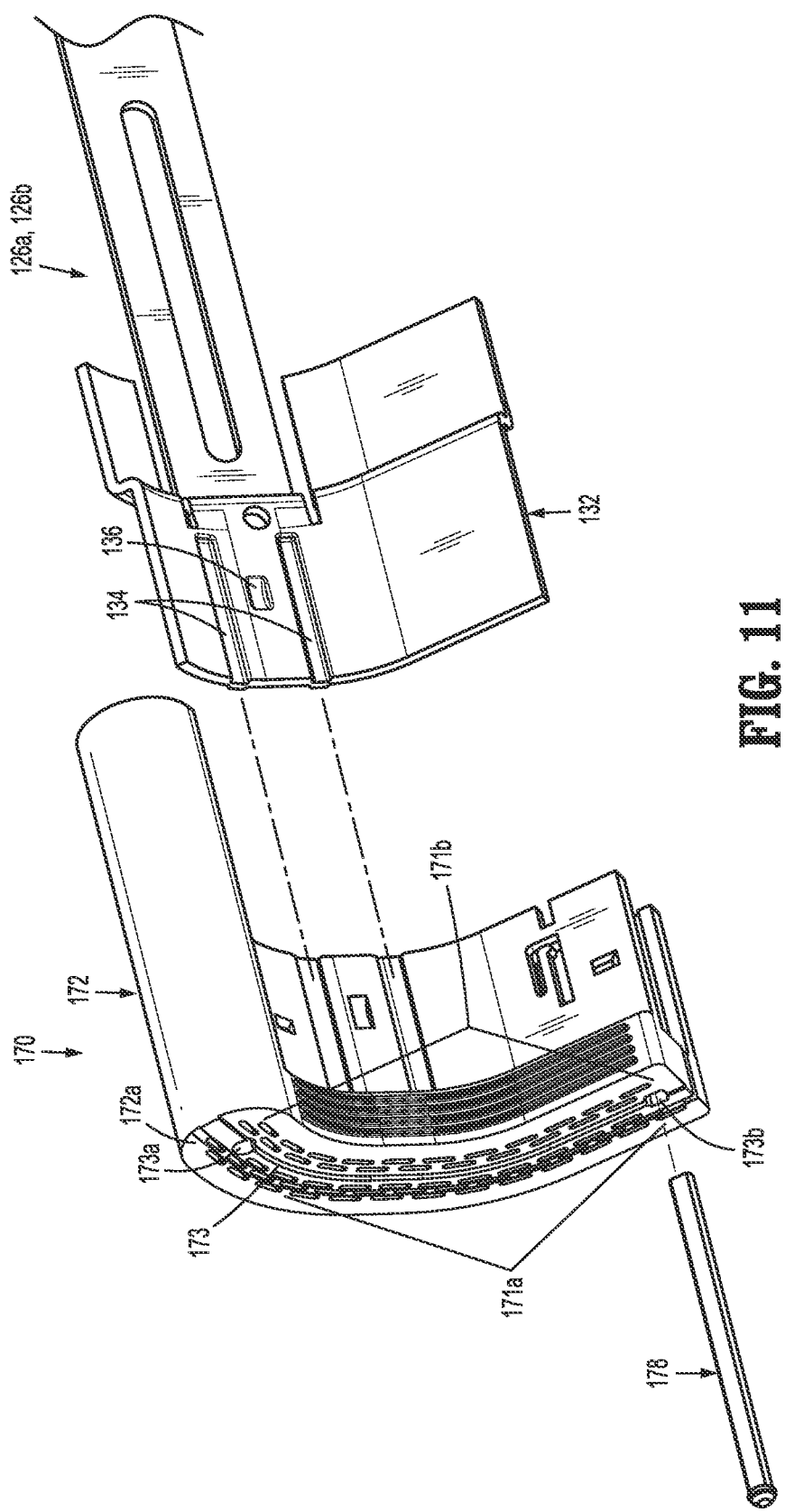
FIG. 11 is a perspective view of a cartridge assembly and clamp slide member of the surgical stapling instrument shown in FIGS. 1-4.

Referring also to FIG. 11, the staple cartridge 172 is configured for operable engagement with the clamp slide members 126a, 126b (only one shown). As described above, the clamp slide members 126a, 126b extend from the handle assembly 110 (FIG. 1) and support the cartridge assembly 170. The head portion 132 of each clamp slide member 132 defines a pair of alignment features 134 to facilitate alignment of the cartridge assembly 170 within the clamp slide members 126a, 126b, and a tab 136 to provide a snap fit connection with the clamp slide members 126a, 126b. Although shown with a pair of alignment features 134 and a single tab 136, it is envisioned that the head portion 132 of the clamp slide members 126a, 126b may include any number of alignment features 134 and/or tabs 136 in any suitable configuration.

With reference now to FIGS. 12 and 13, a staple pusher assembly 174 is slidably disposed within the staple cartridge 172 and engageable by the knife pusher 176. The staple pusher assembly 174 includes a plurality of fingers 174a (FIG. 12), 174b (FIG. 13) configured to be slidably received within respective staple receiving slots 171a, 171b (FIG. 11) of the staple cartridge 172 of the cartridge assembly 170. The fingers 174a, 174b are positioned behind staples "S" (FIG. 4) in respective staple receiving slots 171a, 171b such that advancement of the staple pusher assembly 174 effects advancement of staples "S" from respective staple receiving slots 171a, 171b and into contact with the anvil member 164 of the anvil assembly 160.

A knife member 176a extends distally from the knife pusher 176 and is disposed proximally of the staple pusher assembly 174. The knife pusher 176 is configured to be engaged by the thrust bar 130 and includes a plurality of clips 175 configured to engage tabs 130b formed on a head portion 130a of the thrust bar 130. The clips 175 secure the knife pusher 176 to the thrust bar 130.

In operation, when the thrust bar 130 is advanced into engagement with the staple pusher assembly 174, the tabs 130b formed on the head portion 130a of the thrust bar 130 are engaged by the clips 175 on the knife pusher 176 to secure the knife pusher 176 to the thrust bar 130. In this manner, when the thrust bar 130 is retracted following the formation of the staples "S" (FIG. 4), the knife pusher 174 is retracted with the thrust bar 130. In some embodiments, the staple pusher assembly 174 may be secured to the knife pusher 176 to permit simultaneous retraction of the staple pusher assembly 174 with the knife pusher 176. Alternatively, and as shown, the staple pusher assembly 174 is separate from the knife pusher 176 such that the knife pusher 176 is retracted independently of the staple pusher assembly 174.

With reference to FIG. 14, as detailed above, the housing 152 of the end effector 150 supports the tissue guard assembly 190. Receipt of the cartridge assembly 170 within the base portion 154 of the housing 152 causes the lock member 184 (FIG. 7) of the interlock assembly 180 (FIG. 7) to disengage from the push member 194 of the tissue guard assembly 190. Once disengaged from the lock member 184 of the interlock assembly 180, the pusher member 194 is moved distally by spring 196 of the tissue guard assembly 190. The pusher member 194 engages the tissue guard 178 disposed within the cartridge assembly 170 such that the tissue guard 178 moves distally with the pusher pin 192 until a distal portion of the tissue guard 178 engages the anvil assembly 160. The tissue guard 178 prevents tissue to be stapled from extending below the staple line of the anvil and cartridge assemblies 160, 170.

Figure 15:
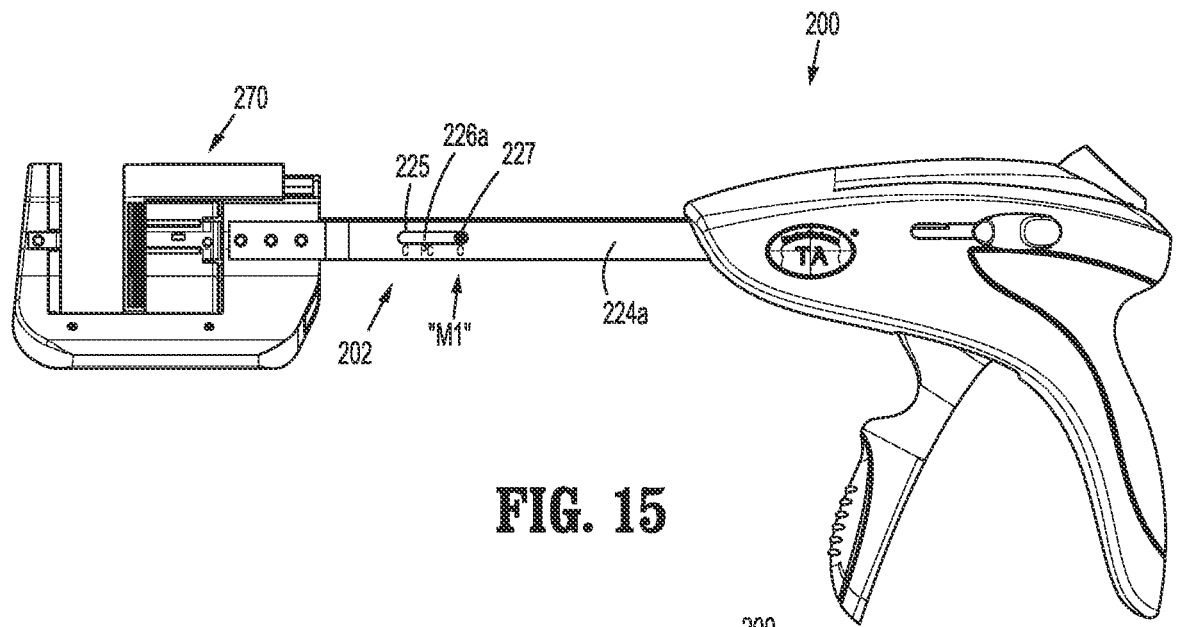
FIG. 15 is a side view of a surgical stapling instrument according another embodiment of the present disclosure, including an indicator mechanism for indicating the position of a cartridge assembly, with a cartridge assembly in an open position.
Figure 16:
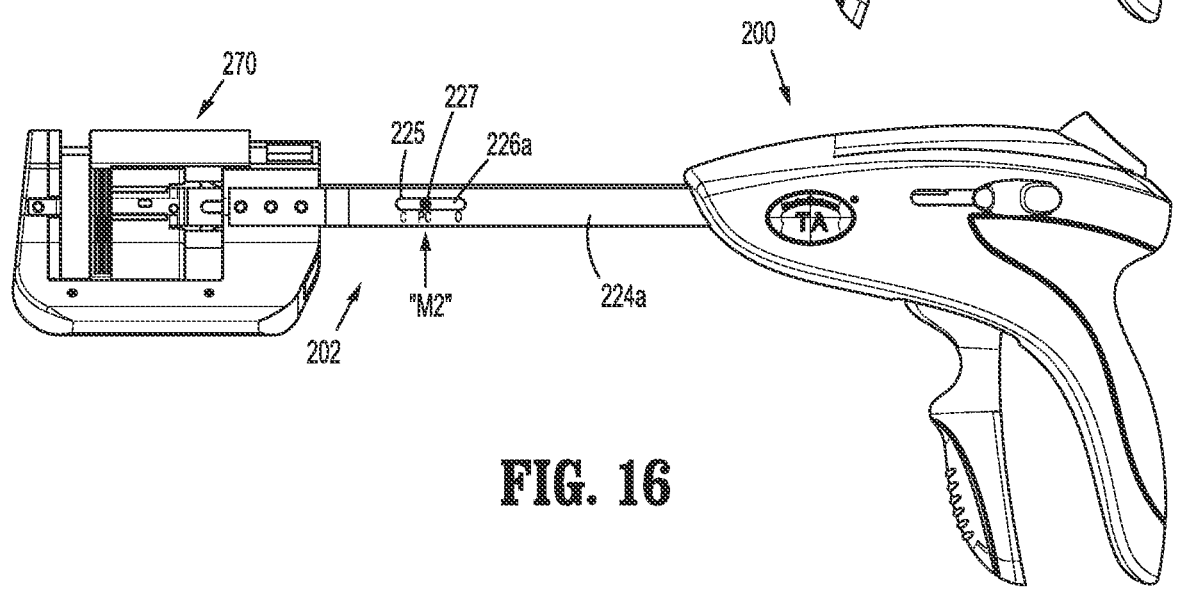
FIG. 16 is a side view of a surgical stapling instrument shown in FIG. 15, with the cartridge assembly in a partially clamped position.
Figure 17:
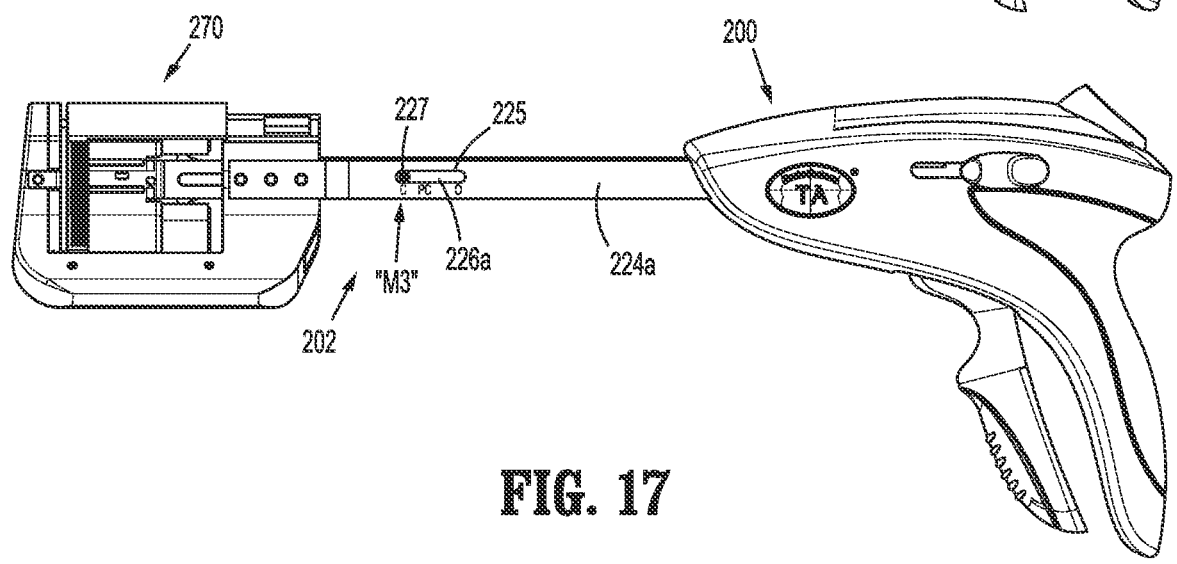
FIG. 17 is a side view of a surgical stapling instrument shown in FIGS. 15 and 16, with the cartridge assembly in the clamped position.

With reference to FIGS. 15-17, a surgical stapling instrument according to another embodiment of the present disclosure, including an indicator feature 202, is shown generally as surgical stapling instrument 200. It is envisioned that the indicator feature 202 can be incorporated into the surgical stapling instruments described herein, and/or be modified for use in surgical stapling instruments having different configurations. The surgical stapling instrument 200 is substantially similar to the surgical stapling instrument 100 described hereinabove, and will only be described to the extent necessary to fully disclose the indicator feature 202. Although shown and described as being formed on only a single side of the surgical stapler 200, it is envisioned that the indicator feature 202 may be included on both sides of the surgical stapling instrument 200.

The surgical stapler 200 includes a first frame member 224 defining a longitudinal slot 225. A first clamp slide member 226 is visible through the longitudinal slot 225. An indicator mark 227 is provided on the first clamp slide member 226a and is disposed such that the indicator mark 227 is positioned at a proximal end of the longitudinal slot 225 when a cartridge assembly 270 of the surgical stapler 200 is in a first or open condition. The first frame member 224 includes a first reference character, mark, and/or symbol "M1" that is aligned with the indicator mark 227 when the cartridge assembly 270 is in an open condition (FIG. 15) indicated to the clinician that the cartridge assembly 270 is in the open condition. In embodiments, the first reference character "M1" is the letter "O", representing "open."

During operation of the surgical stapler 200, the cartridge assembly 270 first moves moved from the open position (FIG. 15) to a partially clamped position (FIG. 16) through advancement of the first clamp slide member 226 in response to actuation of a trigger member 214. As the first clamp slide member 226 moves distally, the indicator mark 227 on the first clamp slide member 226 moves distally within the longitudinal slot 225 of the first frame member 224. The first frame member 224 includes a second reference character, mark, and/or symbol "M2" that aligns with the indicator mark 227 when the cartridge assembly 270 is in the partially clamped position to indicate that the cartridge assembly 270 is in the partially clamped position. In embodiments, the second reference character "M2" is the letters "PC", representing "partially clamped" or "pre-clamped." At this point during a stapling procedure, in embodiments, the trigger member 214 of the surgical stapling instrument 200 is locked, permitting the clinician to verify if the tissue is completely captured between an anvil assembly 260 and the cartridge assembly 270.

Continued advancement of the first clamp slide member 226 causes the cartridge assembly 270 to move to the clamped position in response to continued actuation of the trigger member 214. The first frame member 224 includes a third reference character, mark, and/or symbol "M3" that is aligned with the indicator mark 227 when the cartridge assembly 270 is in a clamped position (FIG. 16) to indicate that the cartridge assembly 270 is in the clamped position. In embodiments, the third reference character "M3" is the letters "C", representing "clamped."

Figure 18:
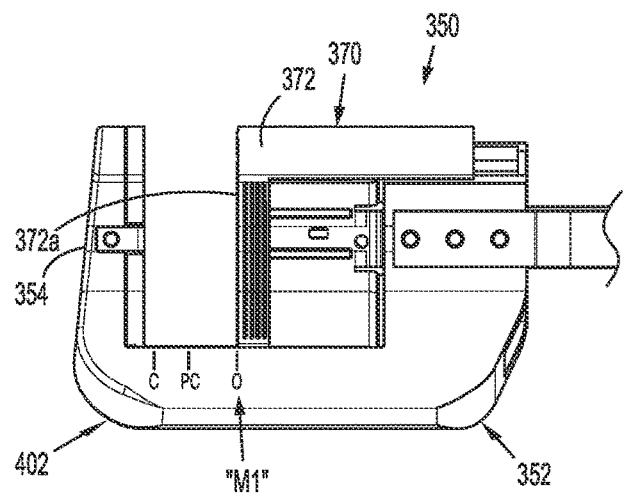
FIG. 18 is a side view of an end effector according to another embodiment of the present disclosure, including an indicator mechanism for indicating the position of the cartridge assembly, with a cartridge assembly in an open position.
Figure 19:
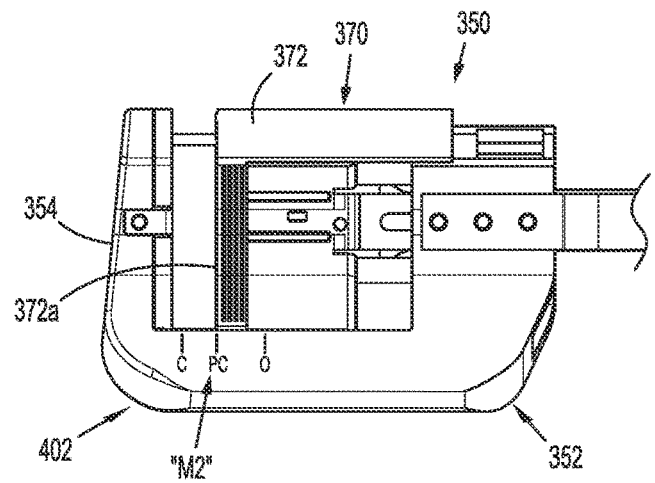
FIG. 19 is a side view of an end effector shown in FIG. 18, with the cartridge assembly in a partially clamped position.
Figure 20:
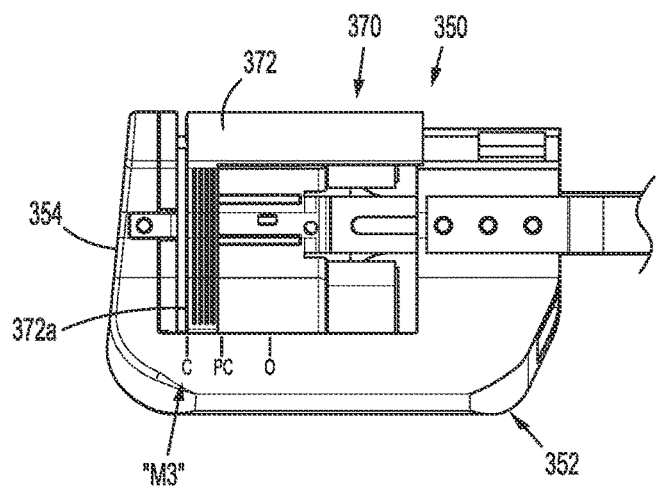
FIG. 20 is a side view of an end effector shown in FIGS. 18 and 19, with the cartridge assembly in a clamped position.

With reference now to FIGS. 18-20, an end effector according to another embodiment of the present disclosure, including an indicator feature 302, is shown generally as end effector 350. The end effector 350 is substantially similar to the end effector 150 described hereinabove, and will only be described to the extent necessary to fully disclose the indicator feature 302. Although shown and described as being formed on only a single side of the end effector 350, it is envisioned that the indicator feature 302 may be included on both sides of the end effector 350.

A jaw portion 354 of a housing 352 of the end effector 350 includes a first reference character, mark, and/or symbol "M1" in line with a distal edge 372a of a staple cartridge 372 of a cartridge assembly 370 of the end effector 350. The first reference character "M1" indicates that the cartridge assembly 270 is in the open condition (FIG. 18). The jaw portion 354 of the housing 352 of the end effector 350 also includes a second reference character, mark, and/or symbol "M2" that is aligned with the distal edge 372a of a staple cartridge 372 of a cartridge assembly 370 when the cartridge assembly 270 is in a partially clamped position to indicate that the cartridge assembly 270 is in the partially clamped position. In addition, the jaw portion 354 of the housing 352 includes a third reference character, mark, and/or symbol "M3" that is aligned with the distal edge 372a of a staple cartridge 372 of a cartridge assembly 370 when the cartridge assembly 270 is in a clamped position (FIG. 19) to indicate that the cartridge assembly 270 is in the clamped position.

Figure 21:
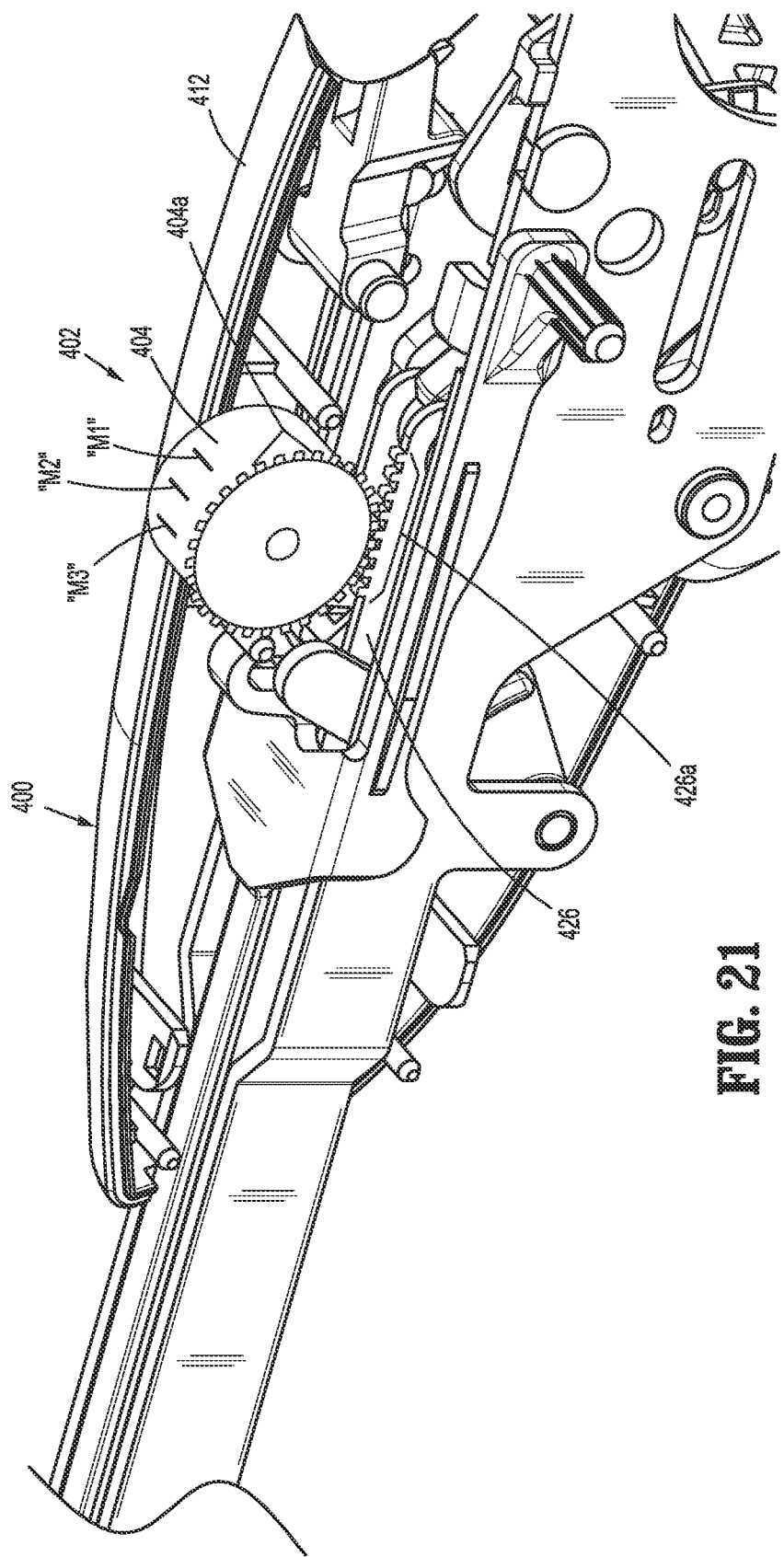
FIG. 21 is a perspective view of an indicator mechanism according to another embodiment of the present disclosure disposed within a handle assembly of a surgical stapling instrument.

Turning now to FIG. 21, a handle assembly 410 of a surgical stapling instrument 400 according to an embodiment of the present disclosure includes an indicator feature 402. The indicator feature 402 includes an indicator member 404 in the form of a wheel member. An outer portion of the indicator member 404 includes a plurality of teeth 404a. The plurality of teeth 404a on the wheel member 404 is configured to engage a plurality of teeth 426a formed on a first clamp slide member 426. The plurality of teeth 404a, 426a of the respective wheel member 404 and first clamp slide member 426 may be configured such that the as the first clamp slide member 426 is translated longitudinally, the wheel member 404 rotates continuously. Alternatively, either or both of the plurality of teeth 404a, 426a of the respective wheel member 404 and the first clamp slide member 426 may be configured such that the wheel member 404 only rotates as a cartridge assembly (not shown) attains a given position, e.g., partially clamped, clamped.

The wheel 404 includes first, second, and third reference characters or marks "M1", "M2", "M3" for indicating the position of a cartridge assembly (not shown) in relation to an anvil assembly (not shown). As the first clamp slide member 226 advances distally to move the cartridge assembly from an open position, to a partially clamped position, to the clamped position, the wheel member 404 is rotated via contact between the plurality of teeth 426a on first clamp slide member 426 and the plurality of teeth 404a on the wheel member 404 to align the first, second, or third reference character "M1", "M2", "M3" with a mark (not shown) on the stationary handle 412, or with a viewing window (not shown) of the stationary handle 412, to indicate to a clinician the position of the cartridge assembly.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

The invention claimed is:

1. A surgical stapling instrument comprising:
    an elongated body portion having a distal portion and defining a longitudinal axis; and
    an end effector supported on the distal portion of the elongated body portion, the end effector including:
        a curved anvil assembly; and
        a curved cartridge assembly coupled to the curved anvil assembly, and defining first and second arrays of staples receiving slots and a knife receiving slot, the first array of staple receiving slots consisting of three rows of staple receiving slots and the second array of staple receiving slots consisting of two rows of staple receiving slots, each slot of the first and second arrays of staple receiving slots receiving a staple, the first array of staple receiving slots formed radially outwardly of the knife receiving slot and the second array of staple receiving slots formed radially inwardly of the knife receiving slot, wherein a height of the staples in each row of the three rows of staple receiving slots of the first array of staple receiving slots is different than the height of the staples in each of the other rows of the three rows of staple receiving slots of the first array of staple receiving slots.

2. The surgical stapling instrument of claim 1, wherein the cartridge assembly includes a staple cartridge and a tissue guard that is extendable from the staple cartridge.

3. The surgical stapling instrument of claim 2, wherein the end effector includes a tissue guard assembly configured to advance the tissue guard into contact with the anvil assembly when the cartridge assembly is secured to the housing of the end effector.

4. The surgical stapling instrument of claim 2, wherein the end effector is secured to the distal portion of the elongated body portion by rivets.

5. The surgical stapling instrument of claim 1, further including an indicator feature supported on the elongated body portion for indicating to a clinician a position of the cartridge assembly relative to the anvil assembly.

6. The surgical stapling instrument of claim 1, wherein the height of the staples in a row of the first array of staple receiving slots closest to the knife receiving slot is shorter than a height of the staples in a row of the first array of stapling receiving slots furthest from the knife receiving slot.

7. An end effector for a surgical stapler, the end effector comprising:
- a curved anvil assembly; and
- a curved cartridge assembly moveable in relation to the curved anvil assembly, and defining first and second arrays of staples receiving slots and a knife receiving slot, the first array of staple receiving slots consisting of three rows of staple receiving slots and the second array of staple receiving slots consisting of two rows of staple receiving slots, each slot of the first and second arrays of staple receiving slots receiving a staple, the first array of staple receiving slots formed radially outwardly of the knife receiving slot and the second array of staple receiving slots formed radially inwardly of the knife receiving slot, wherein a height of the staples in each row of the three rows of staple receiving slots of the first array of staple receiving slots is different than the height of the staples in each of the other rows of the three rows of staple receiving slots of the first array of staple receiving slots.

8. The end effector of claim 7, wherein a height of the staples in a row of the first array of staple receiving slots closest to the knife receiving slot is shorter than a height of the staples in a row of the first array of stapling receiving slots furthest from the knife receiving slot.

9. A cartridge assembly comprising:
- a curved staple cartridge defining:
  - a knife receiving slot;
  - a first array of staple receiving slots consisting of three rows of staple slots; and
  - a second array of staple receiving slots consisting of two rows of staple slots, each slot of the first and second arrays of staple receiving slots receiving a staple, the first array of staple receiving slots formed radially outwardly of the knife receiving slot and the second array of staple receiving slots formed radially inwardly of the knife receiving slot, wherein a height of the staples in each row of the three rows of staple receiving slots of the first array of staple receiving slots is different than the height of the staples in each of the other rows of the three rows of staple receiving slots of the first array of staple receiving slots.

10. The cartridge assembly of claim 9, wherein the height of the staples in a row of the first array of staple receiving slots closest to the knife receiving slot is shorter than the height of the staples in a row of the first array of stapling receiving slots furthest from the knife receiving slot.

\* \* \* \* \*